(12) United States Patent
Rieck et al.

(10) Patent No.: US 10,548,315 B2
(45) Date of Patent: Feb. 4, 2020

(54) USE OF SUCCINATE DEHYDROGENASE INHIBITORS FOR EXTENDING SHELF LIFE OF FRUITS AND VEGETABLES

(75) Inventors: Heiko Rieck, Burscheid (DE); Hélène Lachaise, Lyons (FR); Gilbert Labourdette, Paray le Monial (FR); Pete Howard Davies, Muntinlupa (PH); Dominique Steiger, Düsseldorf (DE); Luk De Maeyer, Linter-Diegem (BE); George Hauley Musson, IV, Raleigh, NC (US); Lorianne Fought, Kerman, CA (US); Sylvain Tafforeau, Lyons (FR)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 236 days.

(21) Appl. No.: 12/705,058

(22) Filed: Feb. 12, 2010

(65) Prior Publication Data
US 2010/0292080 A1  Nov. 18, 2010

Related U.S. Application Data

(60) Provisional application No. 61/258,796, filed on Nov. 6, 2009.

(30) Foreign Application Priority Data

Feb. 13, 2009 (EP) .................................. 09356008

(51) Int. Cl.
*A01N 43/40* (2006.01)
*A01N 37/50* (2006.01)
*A01N 43/54* (2006.01)

(52) U.S. Cl.
CPC .................................. *A01N 43/40* (2013.01)

(58) Field of Classification Search
CPC combination set(s) only.
See application file for complete search history.

(56) References Cited

U.S. PATENT DOCUMENTS

| | | | |
|---|---|---|---|
| 1,774,866 A | 9/1930 | Beadle | |
| 2,213,557 A | 9/1940 | Tisdale et al. | |
| 2,282,801 A | 5/1942 | Musher | |
| 2,364,614 A | 12/1944 | Harold | |
| 2,373,521 A | 4/1945 | Wigelsworth | |
| 2,470,281 A | 5/1949 | Allingham | |
| 2,515,025 A | 7/1950 | Laszlo et al. | |
| 2,560,820 A | 7/1951 | Recker | |
| 2,703,760 A | 3/1955 | George | |
| 3,410,696 A | 11/1968 | Rosenfield | |
| 3,451,826 A | 6/1969 | Mulder | |
| 3,461,304 A | 8/1969 | Genahr et al. | |
| 3,471,303 A | 10/1969 | Hamdy et al. | |
| 3,556,814 A | 1/1971 | Whitman et al. | |
| 3,669,691 A | 6/1972 | Long et al. | |
| 3,801,715 A | 4/1974 | Smith et al. | |
| 3,973,047 A | 8/1976 | Linaberry et al. | |
| 3,997,674 A | 12/1976 | Ukai et al. | |
| 4,338,342 A | 7/1982 | Tan et al. | |
| 4,344,971 A | 8/1982 | Garbutt | |
| 2007/0105915 A1* | 5/2007 | Gouot | A01N 43/40 514/357 |
| 2010/0105670 A1* | 4/2010 | Hong et al. | 514/230.5 |

FOREIGN PATENT DOCUMENTS

| | | |
|---|---|---|
| EP | 0737682 | 10/1996 |
| EP | 2036438 | 3/2009 |
| WO | 03010149 | 2/2003 |
| WO | 03/074491 | 9/2003 |
| WO | 2004016088 | 2/2004 |
| WO | 2004/035589 | 4/2004 |
| WO | 2006/015865 | 2/2006 |
| WO | 2006/015866 | 2/2006 |
| WO | 2006/087343 | 8/2006 |
| WO | 2006/114574 A2 | 11/2006 |

OTHER PUBLICATIONS

Schirra et al., Residues of the Quinone outside inhibitor fungicide trifloxystrobin after postharvest dip treatment to control *Penicillium* spp. Oon citrus fruit, 2006, Journal of food protection, vol. 69, No. 7, pp. 1646-1652.*
EPA Flint Fungicide label letter (May 21, 2008).*
Mertely, J.C. et al., "Timing of fungicide applications for Botrytis cinerea based on development stage of strawberry flowers and fruit," Plant Disease, vol. 86, No. 9, pp. 1019-1024 (2002).*

* cited by examiner

*Primary Examiner* — John Pak
(74) *Attorney, Agent, or Firm* — McBee Moore & Vanik IP, LLC

(57) ABSTRACT

The present invention relates to the use of succinate dehydrogenase Inhibitors for extending shelf life and storage stability of fruits and vegetables, to a method for extending shelf life of fruits and vegetables by applying a succinate dehydrogenase inhibitor to the crops prior to the harvest of the fruits or vegetables and to a fruit or vegetable treated with a succinate dehydrogenase Inhibitor.

14 Claims, 3 Drawing Sheets

USE OF SUCCINATE DEHYDROGENASE INHIBITORS FOR EXTENDING SHELF LIFE OF FRUITS AND VEGETABLES

CROSS REFERENCE TO RELATED APPLICATION

This application claims priority to EP 09356008.4 filed Feb. 13, 2009 and U.S. Provisional Application 61/258,796 filed Nov. 6, 2009, the contents of which are incorporated herein by reference in their entireties.

BACKGROUND

Field of the Invention

The present invention relates to the use of succinate dehydrogenase Inhibitors for extending shelf life and storage stability of fruits and vegetables and to a method for extending shelf life of fruits and vegetables by applying a succinate dehydrogenase inhibitor to the crops prior to the harvest of the fruits or vegetables.

Description of Related Art

Fresh fruits and vegetables are extremely perishable commodities. Heretofore many techniques have been employed to protect such food products from oxidative degradation, mold attack and moisture penetration and to preserve the freshness, texture and color of the fresh produce.

One of the earliest means of lengthening the shelf life of fruits and vegetables was refrigeration. However, most fresh produce when stored under reduced temperatures for prolonged periods shows adverse effects on the taste, odor or quality of the product from microbial and mold growth above 1,7° C. In addition, storage temperatures below 1,7° C. often show chill injury to the tissue of the produce. Hence, in many instances refrigeration alone is not effective in achieving the desired shelf life for a particular fruit or vegetable.

Coating fresh fruits and/or vegetables is another of these techniques which has been employed with varying degrees of success. Not only must the coating be effective in prolonging the useful shelf life of the fresh product, but the appearance of the commodity must not be altered from that of its natural state. At a minimum, this natural appearance must not only remain unchanged but should ideally be enhanced especially when the fruit or vegetable will be displayed for sale. The selection of a coating material is further complicated where the fruit or vegetable is to be consumed in its natural state and it is considered essential that there be no need to remove the coating. In that event, the coating material must not only be edible, it must not affect or alter the natural organoleptic characteristics of the fresh fruit or vegetable.

Typical of these prior art coatings are the wax emulsions of U.S. Pat. No. 2,560,820 of Recker and U.S. Pat. No. 2,703,760 of Cunning Coatings of natural materials have been employed including milk whey (U.S. Pat. No. 2,282, 801 of Musher), lecithin (U.S. Pat. No. 2,470,281 of Allingham and U.S. Pat. No.3,451,826 of Mulder), gelatin together with polyhydric alcohol (U.S. Pat. No. 3,556,814 of Whitman et al.) and protein (U.S. Pat. No. 4,344,971 of Garbutt). Polymers have also been used extensively, viz., a thermoplastic polymer (U.S. Pat. No. 2,213,557 of Tisdale et al.), vinyl acetate polymer (U.S. Pat. No. 3,410,696 of Rosenfield), a hydrophilic polymer (U.S. Pat. No. 3,669,691 of De Long et al.) and the combination of a water soluble polymer and a hydrophobic material (U.S. Pat. No. 3,997,674 of Ukai et al.). Cellulostic materials have found utility in coating fruits and vegetables including hydrated cellulose (U.S. Pat. No. 1,774,866 of Beadle), a combination of cellulose and wax (U.S. Pat. No. 2,364,614 of Beatty), cellulose ether in combination with a fatty acid ester (U.S. Pat. No. 3,471,303 of Hamdy et al.) or monoglyceride and a fatty acid metal salt (U.S. Pat. No. 3,461,304 of Hamdy et al.), or a sucrose ester of a fatty acid (U.S. Pat. No. 4,338,342 of Tan et al.)

Food preservation has for many years employed such mutually exclusive processes as dehydration and freezing. Both of these operations often include a heat treatment, known as blanching, which is conducted prior to the dehydration or freezing step. Blanching is said to reduce enzyme or bacteria level and to prevent or minimize undesirable changes during storage in the dry or frozen state, such as changes in color, odor or texture or loss of vitamins. Blanching may be conducted with steam (e.g., U.S. Pat. No. 2,373,521 of Wigelsworth), hot water (U.S. Pat. No. 2,515, 025 of Vahl et al.), hot oxygen-free gas (U.S. Pat. No. 3,801,715 of Smith et al.) or hot air (U.S. Pat. No. 3,973,047 of Linaberry et al.).

The later published prior art reference EP-A-2036438 discloses the postharvest use of different succinate dehydrogenase inhibitors for improving the shelf life of fruits and vegetables. However, preharvest treatment is not disclosed in the reference.

WO 2004/016088 teaches the preharvest application of fluopyram in order to control *Botrytis cinerea* in cucumbers.

Blacharski, R.; Legard, D.; Bartz,: "The Effect of Preharvest Fungicide Applications on Control of Postharvest Disease" [Online] 1999, XP002536551 teaches the preharvest application of protective fungicides such as captan and thiram to control postharvest occurrence of *Botrytis cinerea* in strawberries, thereby extending the shelf life of the fruits.

Therefore, there is a strong need for methods for further improving shelf life of fruits and vegetables which avoid the drawbacks resulting from the prior art methods.

SUMMARY

The problem outlined above has been solved by the use of succinate dehydrogenase inhibitors for extending shelf life of fruits and vegetables, wherein the succinate dehydrogenase inhibitor was applied to the crop prior to the harvest of the fruits or vegetables.

It has surprisingly been found that the application of succinate dehydrogenase inhibitors during the growing and maturation periods avoids development of bacterial or fungal diseases during the storage period. This effect was especially notable with the reduction of one of the major fungus causing post harvest problems, i.e. *Rhizopus* spp., *Sclerotinia minor* and *Sclerotinia sclerotiorium*. Consequently, shelf life and storage stability of the treated fruits and vegetables is significantly extended.

Figure 1:
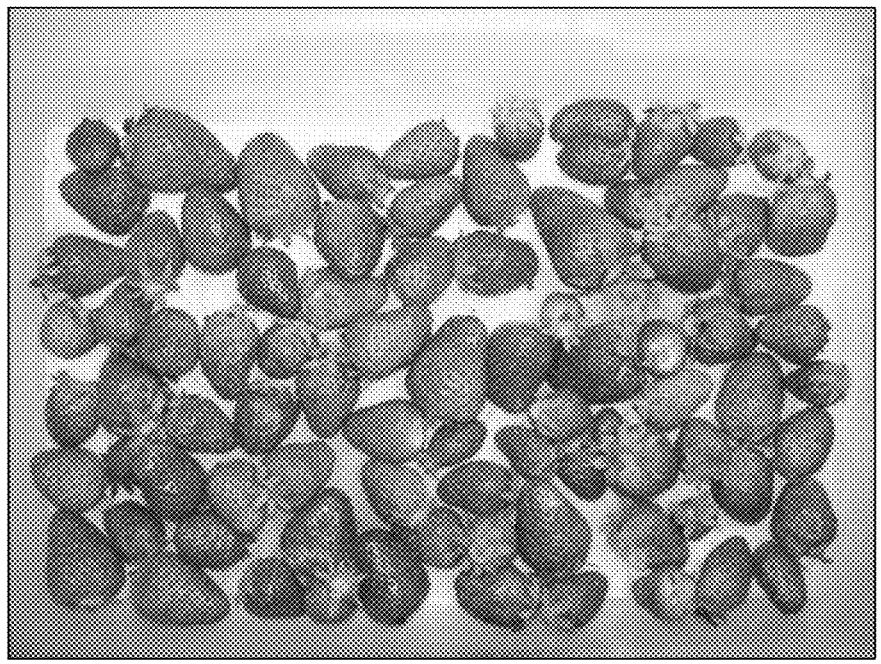
FIG. 1: Photo of a harvest date box for treatment number 3 (FLU+TFS).

The "blank spots" and wet paper were due to the removal of berries that had melted following a *Rhizopus* infection (to prevent a second cycle of infection that would overwhelm the berries in the box). The dark grey fungus developed to cover the berries within a 24-hour period in the box.

DETAILED DESCRIPTION OF A PREFERRED EMBODIMENT

In conjunction with the present invention all active substances (a.s.) which inhibit succinate dehydrogenase in the mitochondrial respiration chain can be used. In a preferred embodiment of the present invention the succinate dehydrogenase inhibitor is selected from the group consisting of fluopyram, isopyrazam, boscalid, penthiopyrad, N-[2-(1,3-dimethylbutyl)phenyl]-5-fluoro-1,3-dimethyl-1H-pyrazole-4-carboxamide, sedaxan and bixafen or mixtures thereof. In a most preferred embodiment of the present invention the succinate dehydrogenase inhibitor is fluopyram.

Fluopyram having the chemical name N-{2-[3-chloro-5-(trifluoromethyl)-2-pyridinyl]ethyl}-2-(trifluoromethyl) benzamide is a fungicide belonging to the chemical class of pyridylethylbenzamides. Fluopyram and its manufacturing process starting from known and commercially available compounds is described in EP-A-1 389 614.

N-[2-(1,3-dimethylbutyl)phenyl]-5-fluoro-1,3-dimethyl-1H-pyrazole-4-carboxamide and its manufacturing process starting from known and commercially available compounds is described in WO 03/010149.

Bixafen having the chemical name N-(3',4'-dichloro-5-fluoro-1,1'-biphenyl-2-yl)-3-(difluoro-methyl)-1-methyl-1H-pyrazole-4-carboxamide (Compound I-2) and its manufacturing process starting from known and commercially available compounds is described in WO 03/070705.

Sedaxane is the mixture of 2 cis-isomers 2'-[(1RS,2RS)-1,1'-bicycloprop-2-yl]-3-(difluoromethyl)-1-methylpyrazole-4-carboxanilide and 2 trans-isomers 2'-[(1RS,2SR)-1,1'-bicycloprop-2-yl]-3-(difluoromethyl)-1-methylpyrazole-4-carboxanilide. Sedaxane and its manufacturing process starting from known and commercially available compounds is described in WO 03/074491, WO 2006/015865 and WO 2006/015866.

Isopyrazam is the mixture of 2 syn-isomers 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 2 anti-isomers 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide.
Isopyrazam and its manufacturing process starting from known and commercially available compounds is described in WO 2004/035589.

Penthiopyrad having the chemical name (RS)-N-[2-(1,3-dimethylbutyl)-3-thienyl]-1-methyl-3-(trifluoromethyl) pyrazole-4-carboxamide and its manufacturing process starting from known and commercially available compounds is described in EP-A-0 737 682.

Boscalid having the chemical name 2-chloro-N-(4'-chlorobiphenyl-2-yl)nicotinamide and its manufacturing process starting from known and commercially available compounds is described in DE-A 195 31 813.

Fluxapyraxad having the chemical name 3-(Difluoromethyl)-1-methyl-N-(3',4',5'-trifluorobiphenyl-2-yl)-1H-pyrazole-4-carboxamide and its manufacturing process starting from known and commercially available compounds is described in WO 2006/087343.

In conjunction with the present invention shelf life (or storability) denotes the period of time during which the perishable fruit or vegetable can be stored refrigerated or un-refrigerated, and remain edible and free from noticeable or harmful degradation or contamination by microorganisms or fungi.

Extension of shelf life denotes an elongation of shelf life of at least several days, preferably of at least one week, most preferably of at least one month.

The use/method according to the present invention can be applied to any kind of fruits and vegetables.

Examples for fruits are banana, blackcurrant, redcurrant, gooseberry, tomato, eggplant, guava, lucuma, chili pepper, pomegranate, kiwifruit, grape, table grapes, pumpkin, gourd, cucumber, melon, orange, lemon, lime, grapefruit, banana, cranberry, blueberry, blackberry, raspberry, boysenberry, hedge apple, pineapple, fig, mulberry, apple, apricot, peach, cherry, sunflower seed, strawberry and plum.

Examples for vegetables are green beans, flower buds, such as: broccoli, cauliflower, globe artichokes; seeds, such as sweetcorn also known as maize; leaves, such as kale, lettuce, collard greens, spinach, beet greens, turnip greens, endive; leaf sheaths, such as leeks; buds, such as Brussels sprouts; stems of leaves, such as celery, rhubarb; stem of a plant when it is still a young shoot, such as asparagus, ginger; underground stem of a plant, also known as a tuber, such as potatoes, Jerusalem artichokes, sweet potato, yam; whole immature plants, such as bean sprouts; Roots, such as carrots, parsnips, beets, radishes, turnips; bulbs, such as onions, garlic, shallots.

In a preferred embodiment strawberries or table grapes are treated with succinate dehydrogenase inhibitors, most preferably with fluopyram in order to improve the shelf live of the harvested fruits.

The succinate dehydrogenase inhibitors, preferably fluopyram, can be employed for extending shelf life of fruits and vegetables within a certain period of time after the treatment of the crops bearing the fruits or vegetables or after treating the fruits or vegetables itself. Generally, the succinate dehydrogenase inhibitor is applied to the crop or to its fruits or vegetables prior to the harvest, more preferably prior to the maturation of fruits and vegetables, most preferably during the plant and fruit growth prior to contamination event.

The period of time within which protection is effected generally extends from 1 hour to 6 months, preferably from 1 week to 1 month after the treatment of the crops or its fruits or vegetables with the active compounds.

When employing the succinate dehydrogenase inhibitors, preferably fluopyram, according to the present invention for extending the self life of the harvested fruits or vegetables, the application rates can be varied within a broad range, depending on the type of application. For foliar applications the application rates of active compound are generally ranging from 1 to 500 g/ha, more preferably from 25 to 250 g/ha, most preferably from 30 to 150 g/ha based upon the pure a.s. (active substance).

According to the present invention the succinate dehydrogenase inhibitor, preferably fluopyram, can be applied to all parts of the plants such as shoot, leaf, flower and root, leaves, needles, stalks, stems, flowers, vegetative buds and flower buds fruiting bodies and fruits.

Plants are understood as meaning, in the present context, all plants and plant populations, such as desired and undesired wild plants or crop plants (including naturally occurring crop plants). Crop plants or crops may be plants which can be obtained by conventional breeding and optimization methods or else by biotechnological and genetic engineering methods or by combinations of these methods, including the transgenic plants and including the plant varieties capable or not capable of being protected by plant breeders' rights.

According to the invention the treatment of the plants with the succinate dehydrogenase inhibitors, preferably fluopyram, is carried out directly by the customary treatment methods, for example by immersion, spraying, vaporizing, fogging, injecting, dripping, drenching, broadcasting or painting. In a preferred embodiment of the invention fluopyram is applied by injecting, dripping, drenching or spraying.

The succinate dehydrogenase inhibitors, preferably fluopyram, can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is liquid solvents, pressurized liquefied gases and/or solid carriers, optionally with the use of surface-active agents, that is emulsifiers and/or dispersants and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants, for example, lignosulphite waste liquors and methylcellulose are suitable.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compounds, preferably between 0.5 and 90 percent by weight, based upon the total formulation.

According to the present invention, the succinate dehydrogenase inhibitors, preferably fluopyram, as such or their formulations, can also be used as a mixture with known fungicides, bactericides, acaricides, nematicides, or insecticides, for example, to broaden the activity spectrum or prevent the development of resistance. In many instances, synergistic effects are obtained, i.e. the activity of the mixture exceeds the activity of the individual components.

A further embodiment of the invention relates to the use of a composition comprising a succinate dehydrogenase inhibitor, preferably fluopyram, and a second fungicide extending shelf life of fruits and vegetables.

Suitable fungicides which can be used in combination with the succinate dehydrogenase inhibitor, preferably with fluopyram are selected from the group consisting of (1) Inhibitors of the nucleic acid synthesis, for example benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.

(2) Inhibitors of the mitosis and cell division, for example benomyl, carbendazim, chlorfenazole, diethofencarb, ethaboxam, fuberidazole, pencycuron, thiabendazole, thiophanate, thiophanate-methyl and zoxamide.

(3) Inhibitors of the respiration, for example diflumetorim as CI-respiration inhibitor; bixafen, boscalid, carboxin, fenfuram, flutolanil, fluopyram, furametpyr, furmecyclox, isopyrazam (9R-component), isopyrazam (9S-component), mepronil, oxycarboxin, penthiopyrad, thifluzamide as CII-respiration inhibitor; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyribencarb, trifloxystrobin as CIII-respiration inhibitor.

(4) Compounds capable to act as an uncoupler, like for example binapacryl, dinocap, fluazinam and meptyldinocap.

(5) Inhibitors of the ATP production, for example fentin acetate, fentin chloride, fentin hydroxide, and silthiofam.

(6) Inhibitors of the amino acid and/or protein biosynthesis, for example andoprim, blasticidin-S, cyprodinil, kasugamycin, kasugamycin hydrochloride hydrate, mepanipyrim and pyrimethanil.

(7) Inhibitors of the signal transduction, for example fenpiclonil, fludioxonil and quinoxyfen.

(8) Inhibitors of the lipid and membrane synthesis, for example biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin.

(9) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole.

(10) Inhibitors of the cell wall synthesis, for example benthiavalicarb, dimethomorph, flumorph, iprovalicarb, mandipropamid, polyoxins, polyoxorim, prothiocarb, validamycin A, and valiphenal.

(11) Inhibitors of the melanine biosynthesis, for example carpropamid, diclocymet, fenoxanil, phthalide, pyroquilon and tricyclazole.

(12) Compounds capable to induce a host defence, like for example acibenzolar-S-methyl, probenazole, and tiadinil.

(13) Compounds capable to have a multisite action, like for example bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.

(14) Further compounds like for example 2,3-dibutyl-6-chlorothieno[2,3-d]pyrimidin-4(3H)-one, ethyl (2Z)-3-amino-2-cyano-3-phenylprop-2-enoate, N-[2-(1,3-dimethylbutyl)phenyl]-5-fluoro-1,3-dimethyl-1H-pyrazole-4-carboxamide, N-{2-[1,1'-bi(cyclopropyl)-2-yl]phenyl}-3-(difluoromethyl)-1-methyl-1H-pyrazole-4-carboxamide, 3-(difluoromethyl)-1-methyl-N-(3',4',5'-trifluorobiphenyl-2-yl)-1H-pyrazole-4-carboxamide, 3-(difluoro-methyl)-N-[4-fluoro-2-(1,1,2,3,3,3-hexafluoropropoxy)phenyl]-1-methyl-1H-pyrazole-4-carboxamide, (2E)-2-(2-{[6-(3-chloro-2-methylphenoxy)-5-fluoropyrimidin-4-yl]oxy}-phenyl)-2-(methoxyimino)-N-methylethanamide, (2E)-2-{2-[({[(2E,3E)-4-(2,6-dichloro-phenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}-imino)methyl]phenyl}ethanamide, (2E)-2-{2-[({[(1E)-1-(3-{[(E)-1-fluoro-2-phenyl-ethenyl]oxy}phenyl)ethylidene]amino}oxy)methyl]phenyl}-2-(methoxyimino)-N-methyl-ethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy]phenyl}imidoformamide, N'-{5-(difluoromethyl)-2-methyl-4-[3-(trimethylsilyl)propoxy]phenyl}-N-ethyl-N-methylimidoformamide, O-{1-[(4-methoxyphenoxy)methyl]-2,2-dimethylpropyl}1H-imidazole-1-carbothioate, N-[2-(4-{[3-(4-chlorophenyl)prop-2-yn-1-yl]oxy}-3-methoxyphenyl)ethyl]-$N^2$-(methylsulfonyl)valinamide, 5-chloro-7-(4-methylpiperidin-1-yl)-6-(2,4,6-trifluoro-phenyl)[1,2,4]triazolo[1,5-a]pyrimidine, 5-amino-1,3,4-thiadiazole-2-thiol, propamocarb-fosetyl, 1-[(4-methoxyphenoxy)methyl]-2,2-dimethylpropyl 1H-imidazole-1-carboxylate, 1-methyl-N-[2-(1,1,2,2-tetrafluoro ethoxy)phenyl]-3-(trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-phenylphenol and salts, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, quinolin-8-ol, quinolin-8-ol sulfate (2:1) (salt), 5-methyl-6-octyl-3,7-dihydro[1,2,4]triazolo[1,5-a]pyrimidin-7-amine, 5-ethyl-6-octyl-3,7-dihydro[1,2,4]triazolo[1,5-a]pyrimidin-7-amine, benthiazole, bethoxazin, capsimycin, carvone, chinomethionat, chloroneb, cufraneb, cyflufenamid, cymoxanil, cyprosulfamide, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, flutianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl isothiocyanate, metrafenone, (5-bromo-2-methoxy-4-methylpyridin-3-yl)(2,3,4-trimethoxy-6-methylphenyl)methanone, mildiomycin, tolnifanide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloro-pyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropyl-methoxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and salts, phenazine-1-carboxylic acid, phenothrin, phosphorous acid and its salts, propamocarb fosetylate, propanosine-sodium, proquinazid, pyrrolnitrine, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'-phenyl-N'-prop-2-yn-1-ylthiophene-2-sulfonohydrazide and zarilamid.

In a preferred embodiment the second fungicide is trifloxystrobin. In a more preferred embodiment of the invention a composition comprising fluopyram and trifloxystrobin is used for extending shelf life of fruits and vegetables, preferably of strawberries.

A further embodiment of the present invention is a method extending shelf life of fruits and vegetables characterized in that, fluopyram was applied to the crop prior to the harvest of the fruits and vegetables.

The present invention is exemplified by the following examples.

EXAMPLES

Example A

Strawberry (*Fragaria* spp.) plots were established 6.1 meters long by 0.5 meters wide, with 2 rows per plot arranged in a randomized complete block design with 4 replications each. Treatments were prepared in a standard water volume of 935 l/ha and applied to plots with a backpack sprayer.

Treatments were:
Check (untreated)
FLU+TFS@4 oz/A (Fluopyram@73 g/ha plus Trifloxystrobine@73 g/ha)
FLU+TFS@5 oz/A (Fluopyram@92 g/ha plus Trifloxystrobine@92 g/ha)
Elevate@16 oz/A (Fenhexamid@560 g/ha)

All ripe berries were collected from the plots 15 times (to establish baseline disease rating) and thereafter three times per week (usually 0 to 4 days after each application) and incubated on paper towels in separate plastic storage boxes at 17° C.

Figure 3:
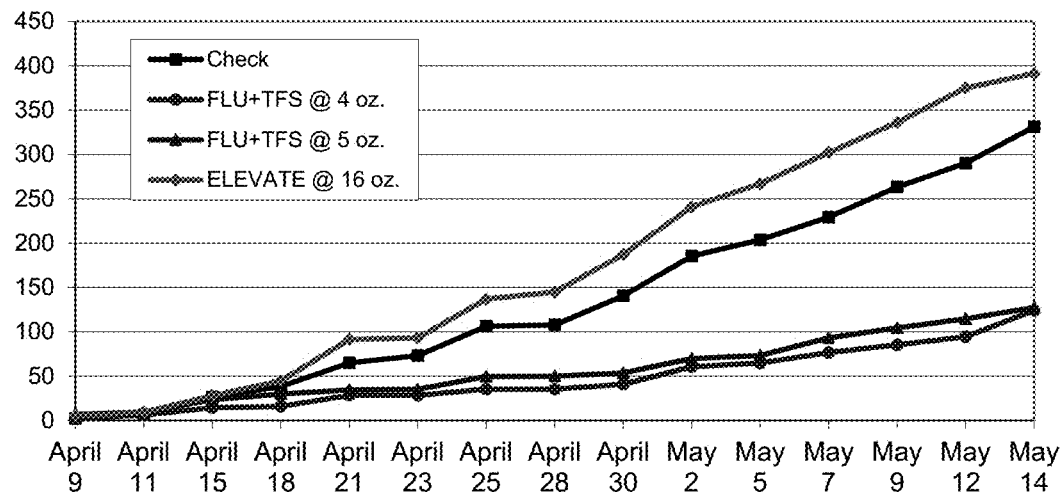
FIG. 3: The figure shows cumulative incidence of berries with visual presence of *Rhizopus stolonifer* infection through 15 harvest dates.
Figure 4:
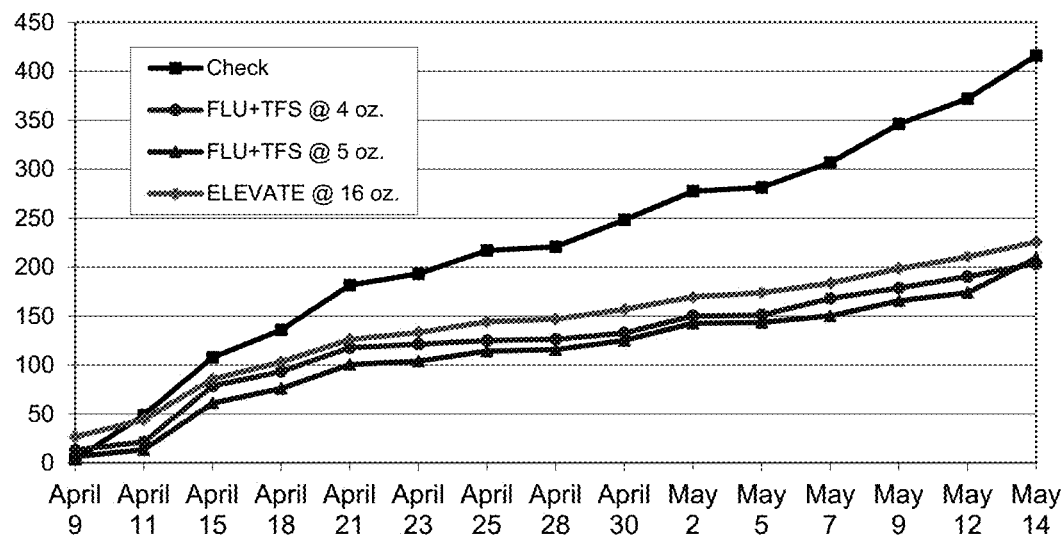
FIG. 4: The figure shows cumulative incidence of berries with visual presence of *Botrytis cinerea* infection through 15 harvest date.
Figure 5:
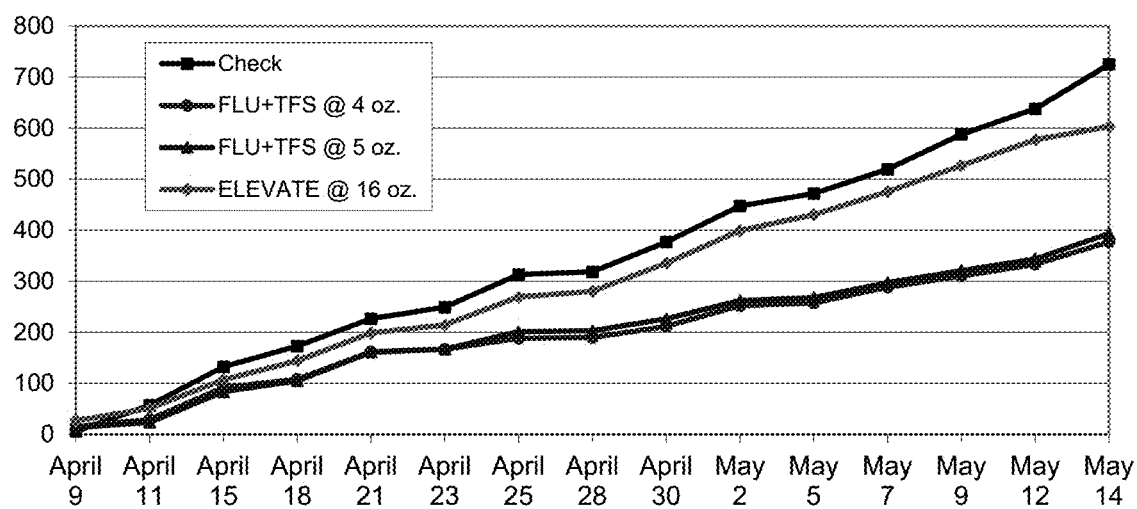
FIG. 5: The figure shows cumulative total disease incidence of berries with visual presence of *Rhizopus stolonifer*, *Botrytis cinerea* and *Penicillium* spp. infection through 15 harvest dates.

Boxes were rated for the three post harvest diseases that developed by counting the number of infected berries per box. As berries melted from disease they were removed from each box to reduce within box contamination between berries (see FIG. 1 and FIG. 2). Data were recorded and graphed below as cumulative incidence of *Rhizopus stolonifera* (see FIG. 3), *Botrytis cinerea* (see FIG. 4), *Penicillium* spp. (see FIG. 5), and cumulative total disease (see Table 1).

Results

Figure 2:
FIG. 2: Photo of a harvest date box for treatment number 4 (Elevate).

The two Fluopyram containing treatments gave excellent control of the post harvest disease Rhizopus stolonifer. At the final rating just over 100 berries were infected compared to between 300 and 400 infected for the check and Elevate treatment. All three fungicides gave excellent control of *Botryts cinerea* compared to the check. Cumulative total post harvest disease (see FIG. 5) was lower for the two Fluopyram treatments (approximately 400 berries) compared to the commercial standard Elevate (approximately 600 berries) and the check (approximately 700berries). The photos in FIGS. 1 and 2 show the diseases on berries and demonstrate the improvement Fluopyram plus Trifloxystrobine treatments give over the currently available mower standard Elevate.

Example B

Green Bean Example

Green beans plots of the variety "Contender" (*Phaseolus vulgaris* L.) were established 4.0 meters long by 1.5 meters wide, with 2 rows per plot arranged in a randomized complete block design with 4 replications each under plastic tunnel Treatments were prepared in a standard water volume of 300 l/ha and applied to plots with a backpack sprayer. Three fungicide applications were made according to the predefined program: first application (A) at beginning of flowering, second application (B) at end of flowering, third application (C) 7 days before harvest.

Treatments were:
1—Untreated check
2—FLU 500 SC@0.5 L/ha (fluopyram@250 g/ha)

At harvest, 30 healthy pods per plot were placed into boxes and stored at room temperature. After 8 days of storage, post-harvest disease was assessed by counting the number of pods presenting symptoms of white mold infection (*Sclerotinia sclerotiorum*).

Results from the post-harvest assessment presented in table 1 as the percentage of damaged pods demonstrate an excellent control of the post-harvest disease with a reduction of 90% of the disease frequency. Although no fungicide application was made after harvest, fluopyram applications during the growing phase of green beans provided a significant extension of the shelf-life of stored beans in comparison to pods from untreated check.

Table 1: control of post-harvest disease caused by *Sclerotinia sclerotiorum* on green beans. Assessment after 8 days storage.

TABLE 1 control of post-harvest disease caused by *Sclerotinia sclerotiorum* on green beans. Assessment after 8 days storage.

| Treatment (dose rate) | % damaged pods (% disease reduction) Mean 4 plots |
|---|---|
| 1 - Untreated check | 17.3 a |
| 2 - FLU 500 SC (0.5 L/ha) | 1.7 (90.1) b |

Means followed by the same letter do not significantly differ (P = 0.05)

Example C

Lettuce Example

Lettuce plots of the iceberg variety "Cam" (*Lactuca sativa* L.) were established in field conditions with 3 replicates and full randomization design. Plots consisted in 4 rows of 5 m length planted within 1.0 m intervals following the farmers practice.

Fungicide treatments were prepared in a standard water volume of 883 l/ha and applied to plots with a backpack sprayer. Three to 5 fungicide applications were made with conventional hand sprayers until the day before harvest.

Application dates: A=x; B=x+13 days; C=x+22 days; D=x+30 days; E=x+36

Treatments were: 1—Untreated check
2—FLU 500 SC@0.5 L/ha (fluopyram@250 g/ha)—5 applications (ABCDE)
3—FLU 500 SC@0.5 L/ha (fluopyram@250 g/ha)—3 applications (ABC)
4—Serenade 10 WP@5.0 Kg/ha (active substance from *Bacillus subtilis*@500 g/ha)—5 applications (ABCDE)

At harvest, all lettuce heads were free of disease. Harvested lettuce heads were wrapped into plastic bags and 3 boxes containing 18 lettuces each (=54 heads) per plot were placed into a climatic chamber at 4° C. during 4 days, then placed at room temperature during 10 days. Assessment of post-harvest diseases was done after this period of 14 days storage by counting the number of lettuces with and without symptoms of *Sclerotinia minor* infections.

Results from post-harvest disease assessment presented in table 2, below, demonstrate a clear effect of fluopyram applications during the growing phase in the field on occurrence of disease symptoms in storage. Either with a sequence of 5 applications (treatment #2) or 3 applications (treatment #3), fluopyram significantly reduced the number of damaged heads by 95.4 and 78.4% compared to untreated check, whereas the reference fungicide did not offer significant control of post-harvest disease. It is therefore concluded that fluopyram sprays applied before harvest reduce the occurrence of post-harvest disease, thus extending the shelf-life of lettuce.

Table 2: control of post harvest disease causes by *Sclerotinia minor* on lettuce heads. Assessment after 14 days of storage.

TABLE 2 control of post-harvest disease caused by *Sclerotinia minor* on lettuce heads. Assessment after 14 days of storage.

| Treatment (dose rate) - application sequence | Number of damaged heads (Mean 3 replicates) | Number of healthy heads (Mean 3 replicates) | % disease reduction (Abbott) |
|---|---|---|---|
| 1 - Untreated check | 15.3 a | 38.7 c | — |
| 2 - FLU 500 SC (0.5 L/ha) - ABCDE | 0.7 c | 53.3 a | 95.4 |
| 3 - FLU 500 SC (0.5 L/ha) - ABC | 3.3 bc | 50.7 ab | 78.4 |
| 4 - Serenade 10 WP (5.0 Kg/ha) - ABCDE | 12.3 a | 41.7 c | 19.6 |

Means followed by the same letter do not significantly differ (P = 0.05)

The invention claimed is:

1. A method for extending shelf life of a strawberry comprising applying fluopyram, and
   i) trifloxystrobin or
   ii) pyrimethanil to a growing strawberry plant prior to harvest of said fruit, to thereby control *Botrytis cinerea, Rhizopus* spp., and/or *Penicillium* spp. that appears on the strawberry fruit post-harvest, wherein the fluopyram is applied at a rate of 25 to 250 g/ha,
   wherein the shelf life of the harvested strawberry is extended at least one week compared to untreated fruits, and
   wherein the method consists of applying a formulation comprising fluopyram and trifloxystrobin or a formulation comprising fluopyram and pyrimethanil during the flowering stage of the plant.

2. A method according to claim 1, wherein fluopyram and trifloxystrobin or pyrimethanil are applied prior to a contamination event.

3. A method according to claim 1, wherein fluopyram is applied to the fruit at a rate of 250 g/ha —based upon the pure active substance.

4. A method according to claim 1, wherein the shelf life is extended at least one month compared to untreated fruits.

5. A method according to claim 1, wherein the formulation comprises 0.5 to 90% by weight of fluopyram.

6. The method of claim 1, wherein the trifloxystrobin is applied at about 73 g/ha or about 92 g/ha.

7. The method of claim 1, wherein the trifloxystrobin is applied.

8. The method of claim 1, wherein the only active substances applied are fluopyram and trifloxystrobin.

9. The method of claim 1, wherein the pyrimethanil is applied.

10. The method of claim 1, wherein the only active substances applied are fluopyram and pyrimethanil.

11. The method of claim 1, further comprising harvesting the strawberry.

12. The method of claim 1, wherein *Botrytis cinerea* is controlled.

13. The method of claim 1, wherein *Rhizopus* spp. is controlled.

14. The method of claim 1, wherein *Penicillium* spp.is controlled.

* * * * *